(12) United States Patent
Servansky

(10) Patent No.: US 9,539,384 B2
(45) Date of Patent: Jan. 10, 2017

(54) TELESCOPING PISTON DRIVE FOR MEDICAL INFUSION DEVICE

(71) Applicant: ANIMAS CORPORATION, West Chester, PA (US)

(72) Inventor: Daniel Servansky, Norristown, PA (US)

(73) Assignee: Animas Corporation, West Chester, PA (US)

(*) Notice: Subject to any disclaimer, the term of this patent is extended or adjusted under 35 U.S.C. 154(b) by 590 days.

(21) Appl. No.: 14/031,344

(22) Filed: Sep. 19, 2013

(65) Prior Publication Data

US 2014/0094754 A1 Apr. 3, 2014

Related U.S. Application Data

(60) Provisional application No. 61/707,079, filed on Sep. 28, 2012.

(51) Int. Cl.
*A61M 5/142* (2006.01)
*A61M 5/145* (2006.01)
*A61M 5/168* (2006.01)
*A61M 5/315* (2006.01)

(52) U.S. Cl.
CPC ..... *A61M 5/14216* (2013.01); *A61M 5/14244* (2013.01); *A61M 5/14566* (2013.01); *A61M 5/1452* (2013.01); *A61M 5/1684* (2013.01); *A61M 2005/16863* (2013.01); *A61M 2005/31518* (2013.01); *A61M 2205/8206* (2013.01)

(58) Field of Classification Search
CPC .............. A61M 5/1456; A61M 5/1452; A61M 5/14566; B05C 17/00576
See application file for complete search history.

(56) References Cited

U.S. PATENT DOCUMENTS

| | | | |
|---|---|---|---|
| 6,248,093 B1* | 6/2001 | Moberg | 604/131 |
| 7,066,909 B1* | 6/2006 | Peter et al. | 604/136 |
| 2003/0009133 A1* | 1/2003 | Ramey | 604/155 |
| 2005/0020980 A1* | 1/2005 | Inoue et al. | 604/152 |
| 2008/0051727 A1* | 2/2008 | Moberg et al. | 604/207 |
| 2009/0326459 A1* | 12/2009 | Shipway et al. | 604/155 |
| 2012/0172817 A1* | 7/2012 | Bruggemann et al. | 604/218 |

* cited by examiner

*Primary Examiner* — Scott Medway

(57) ABSTRACT

Described is a drive mechanism for a drug infusion pump. In one embodiment, an in-line drive mechanism is provided that includes a motor operatively coupled to a lead screw, which is configured to engage a piston. The piston includes a cavity to receive the motor and the lead screw such that the lead screw and at least a portion of the motor are substantially contained within the piston cavity when the piston is in a retracted position. In one embodiment, the motor rotates a drive shaft is configured to turn a mechanism comprising a piston, a lead screw, and a housing that cooperate to extend telescopically to drive a plunger into a medicament cartridge, thereby expelling fluid.

7 Claims, 13 Drawing Sheets

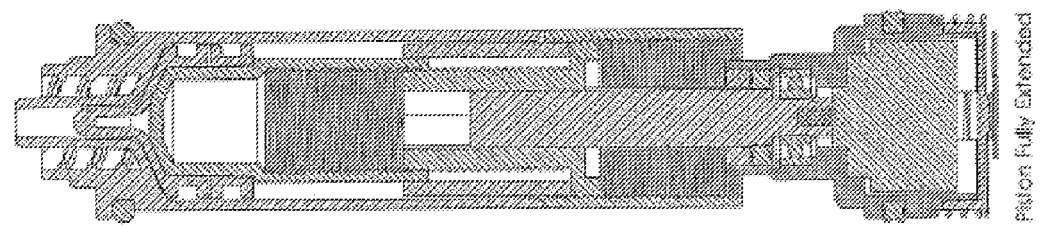
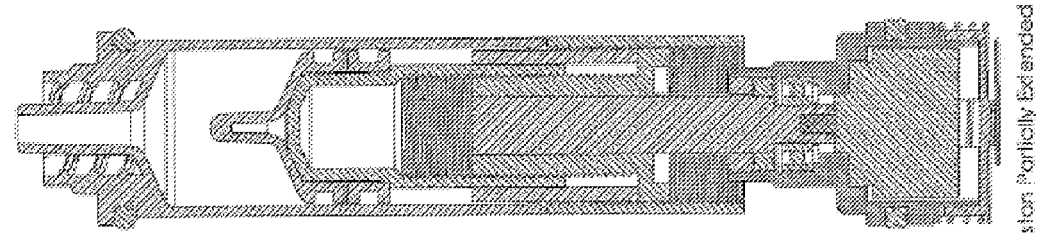
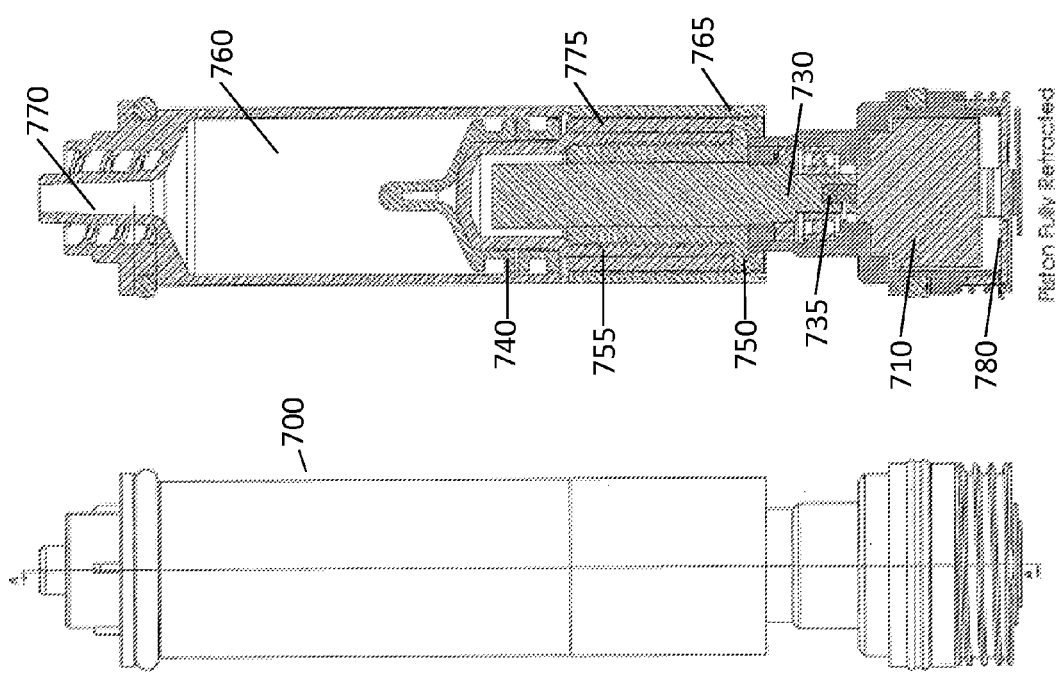

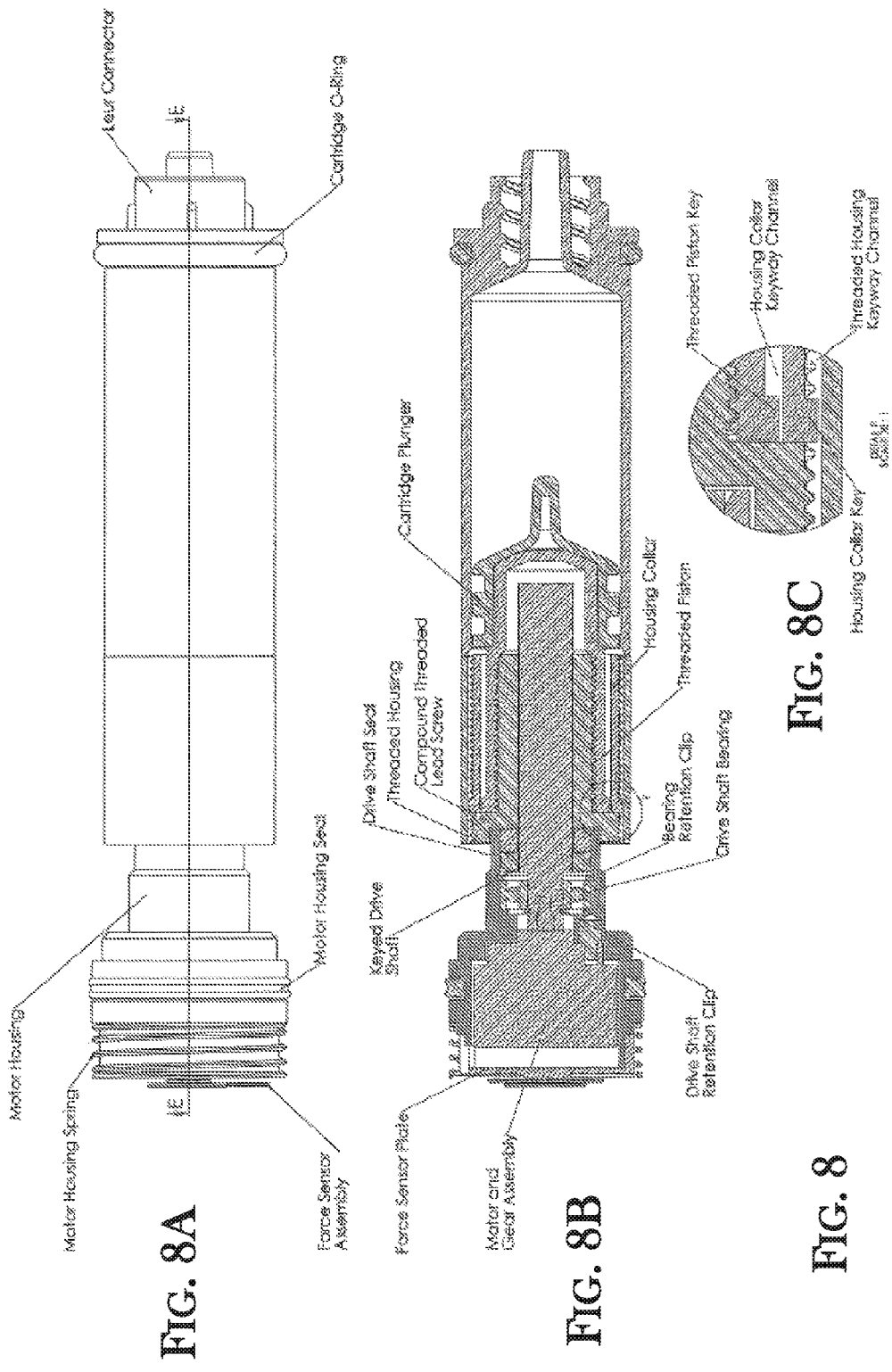

TELESCOPING PISTON DRIVE FOR MEDICAL INFUSION DEVICE

CROSS REFERENCE TO RELATED APPLICATIONS

This application relates to U.S. patent application Ser. No. 61/707,079, filed Sep. 28, 2012; all applications are herein incorporated by reference in their entireties.

FIELD OF THE INVENTION

The present invention relates, in general, to drug delivery devices and, more particularly, to methods for using in-line drive mechanisms within drug delivery devices and methods for their use.

BACKGROUND OF THE INVENTION

The use of drug delivery devices for various types of drug therapy is becoming more common as the automated infusion of a drug may provide more reliable and more precise treatment to a patient.

Diabetes is a major health concern, as it can significantly impede on the freedom of action and lifestyle of persons afflicted with this disease. Typically, treatment of the more severe form of the condition, Type I (insulin-dependent) diabetes, requires one or more insulin injections per day, referred to as multiple daily injections. Insulin is required to control glucose or sugar in the blood, thereby preventing hyperglycemia that, if left uncorrected, can lead to diabetic ketoacidosis. Additionally, improper administration of insulin therapy can result in hypoglycemic episodes, which can cause coma and death. Hyperglycemia in diabetics has been correlated with several long-term effects of diabetes, such as heart disease, atherosclerosis, blindness, stroke, hypertension, and kidney failure.

The value of frequent monitoring of blood glucose as a means to avoid or at least minimize the complications of Type I diabetes is well established. Patients with Type II (non-insulin-dependent) diabetes can also benefit from blood glucose monitoring in the control of their condition by way of diet and exercise. Thus, careful monitoring of blood glucose levels and the ability to accurately and conveniently infuse insulin into the body in a timely manner is a critical component in diabetes care and treatment.

To more effectively control diabetes in a manner that reduces the limitations imposed by this disease on the lifestyle of the affected person, various devices for facilitating blood glucose (BG) monitoring have been introduced. Typically, such devices, or meters, permit the patient to quickly, and with a minimal amount of physical discomfort, obtain a sample of their blood or interstitial fluid that is then analyzed by the meter. In most cases, the meter has a display screen that shows the BG reading for the patient. The patient may then dose theirselves with the appropriate amount, or bolus, of insulin. For many diabetics, this results in having to receive multiple daily injections of insulin. In many cases, these injections are self-administered.

Due to the debilitating effects that abnormal BG levels can have on patients, i.e., hyperglycemia, persons experiencing certain symptoms of diabetes may not be in a situation where they can safely and accurately self-administer a bolus of insulin. Moreover, persons with active lifestyles find it extremely inconvenient and imposing to have to use multiple daily injections of insulin to control their blood sugar levels, as this may interfere or prohibit their ability to engage in certain activities. For others with diabetes, multiple daily injections may simply not be the most effective means for controlling their BG levels. Thus, to further improve both accuracy and convenience for the patient, insulin infusion pumps have been developed.

Insulin pumps are generally devices that are worn on the patient's body, either above or below their clothing. Because the pumps are worn on the patient's body, a small and unobtrusive device is desirable. Therefore, it would be desirable for patients to have a more compact drug delivery device that delivers medication reliably and accurately.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 7A-7D illustrates in cross-sectional view, an embodiment of the invention showing a drive mechanism with a telescoping piston at various states of extension.

FIGS. 8A-8C show cross sectional views of the drive mechanism and telescoping piston of embodiments of the present invention.

DETAILED DESCRIPTION OF ILLUSTRATIVE EMBODIMENTS OF THE INVENTION

Figure 1A:
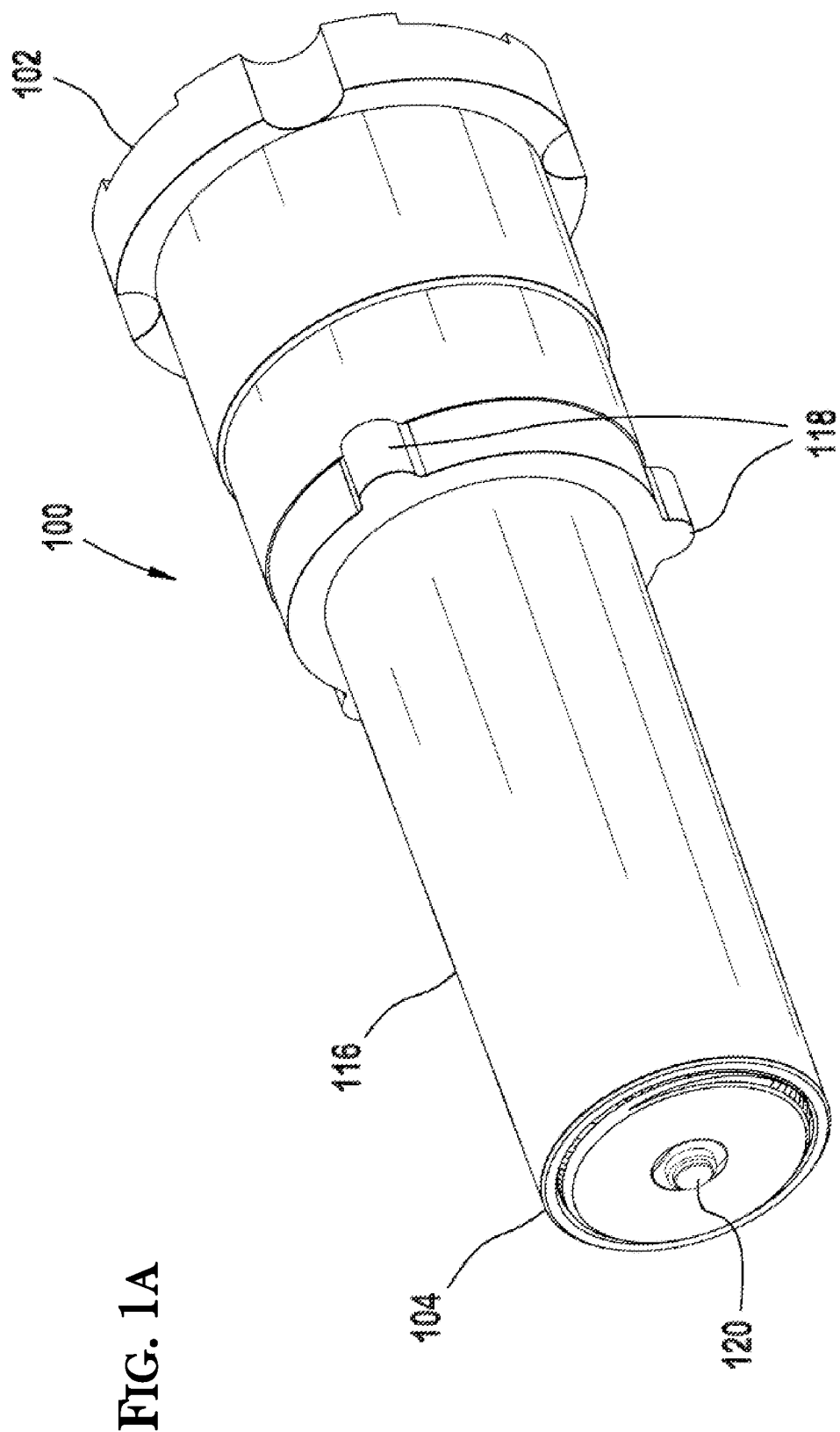
FIGS. 1A and 1B are perspective and cross-sectional perspective views, respectively, of an in-line drive mechanism according to an exemplary embodiment of the present invention in which the drive mechanism is in a retracted position.
Figure 1B:
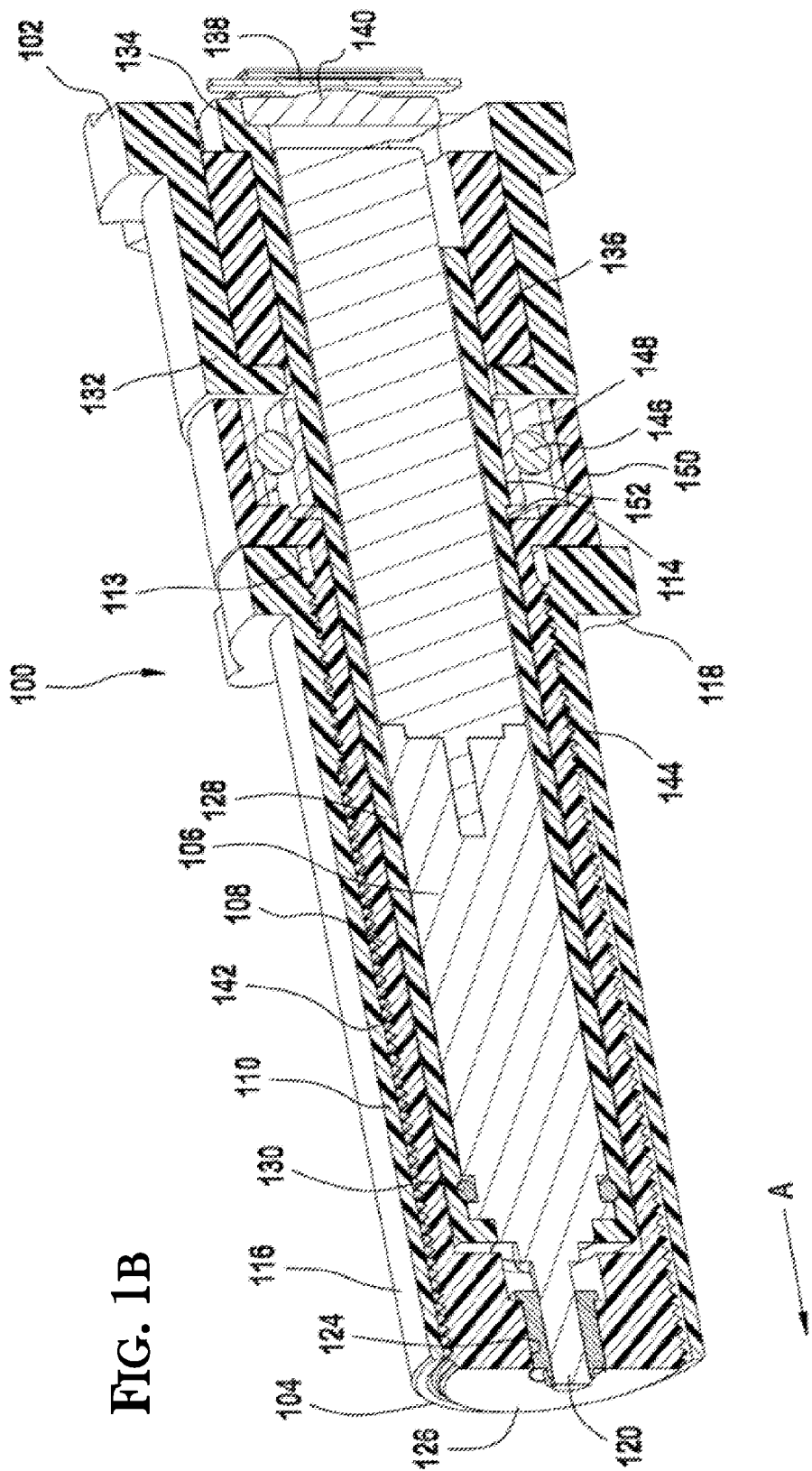
Figure 2:
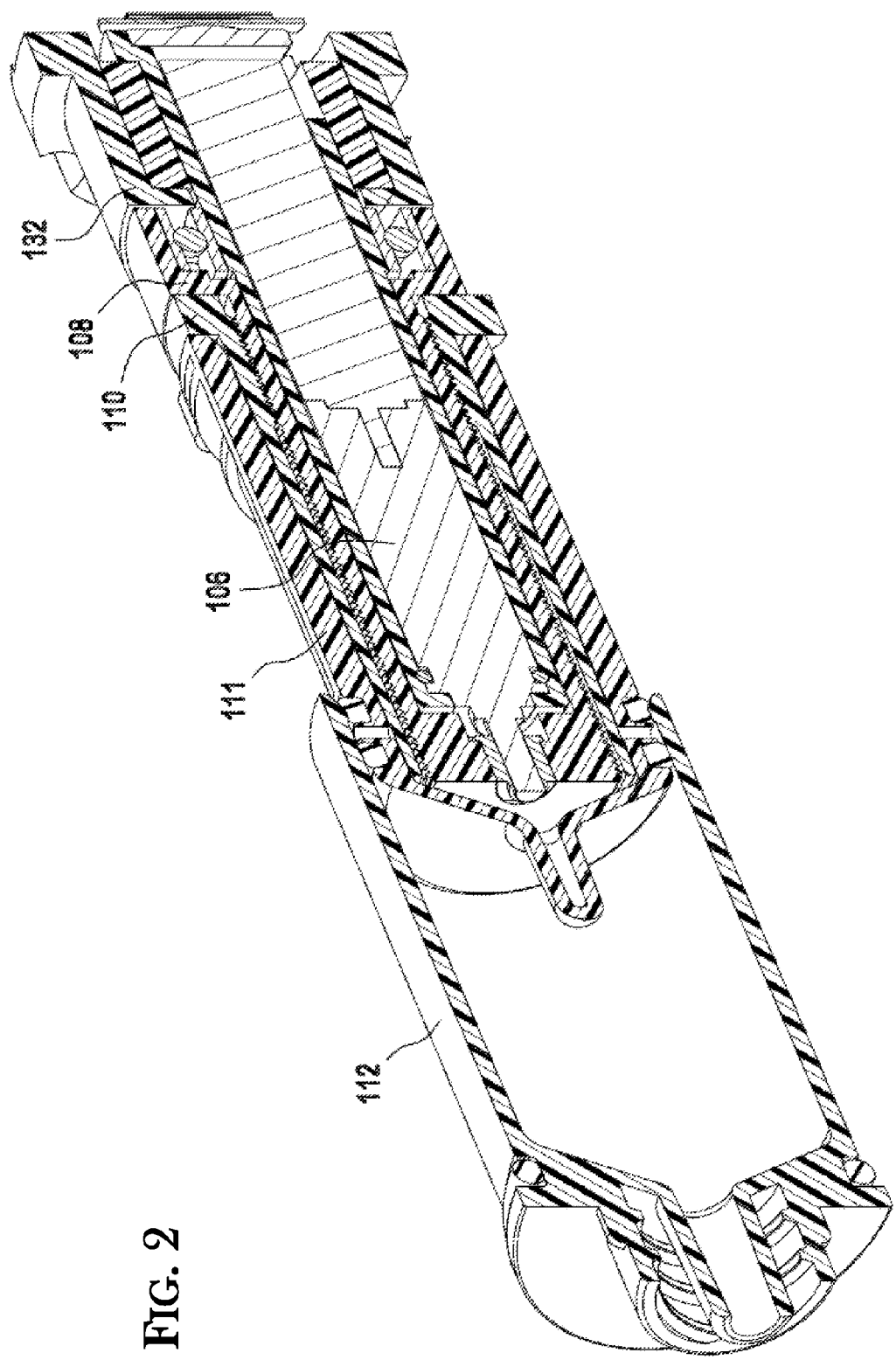
FIG. 2 is a cross-sectional perspective view of the in-line drive mechanism illustrated in FIGS. 1A and 1B engaged with a plunger that is inserted into a drug reservoir.
Figure 3:
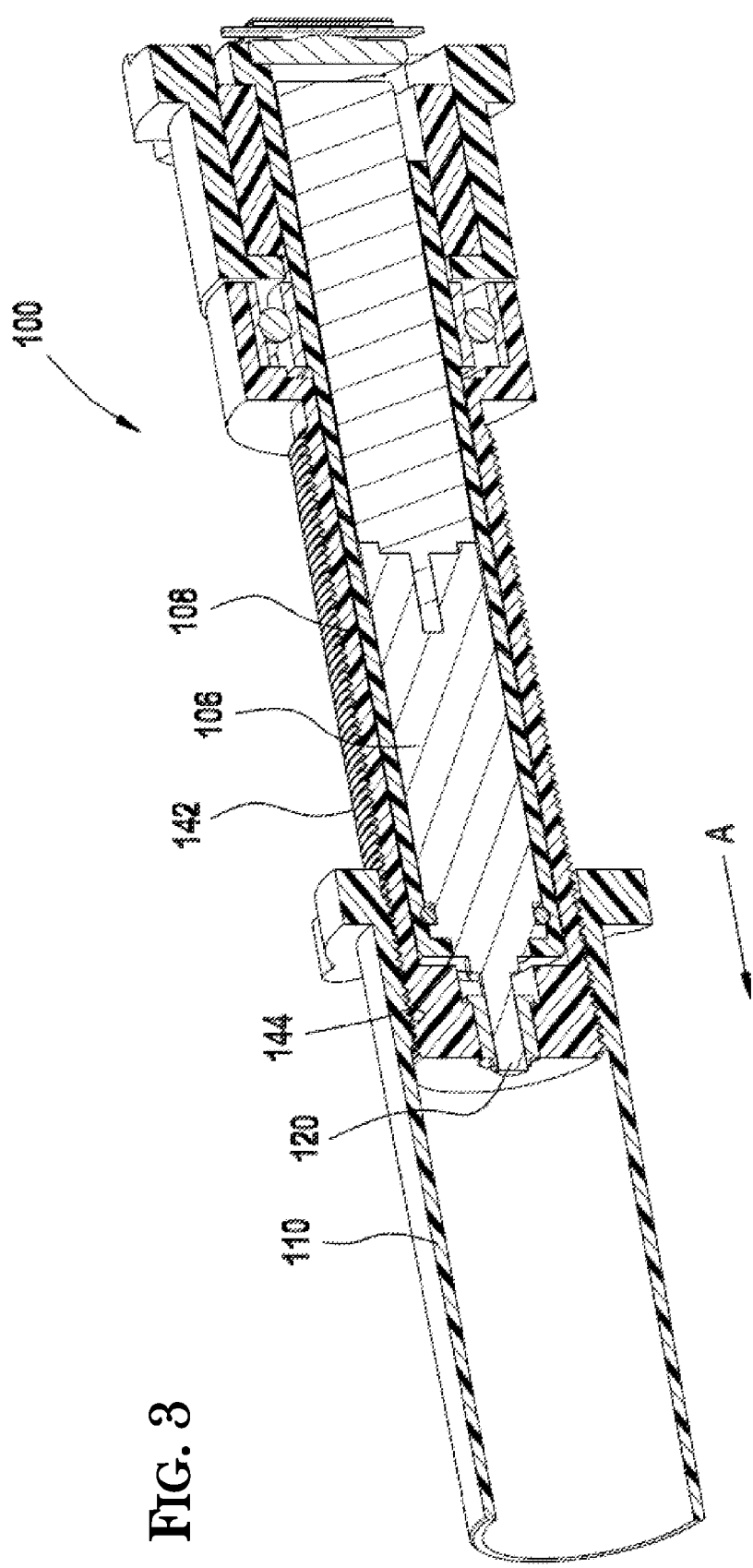
FIG. 3 is a cross-sectional perspective view of the in-line drive mechanism illustrated in FIGS. 1A and 1B with the piston extended.
Figure 4A:
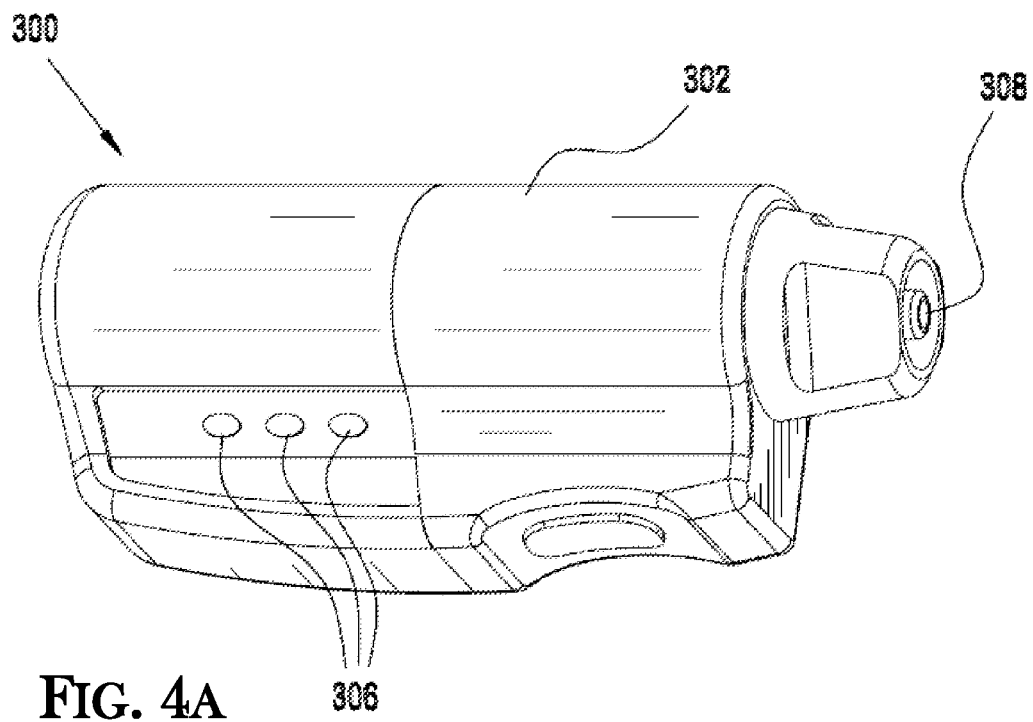
FIGS. 4A and 4B are simplified perspective views of drug delivery devices that are suitable for use with embodiments of the present invention.
Figure 4B:
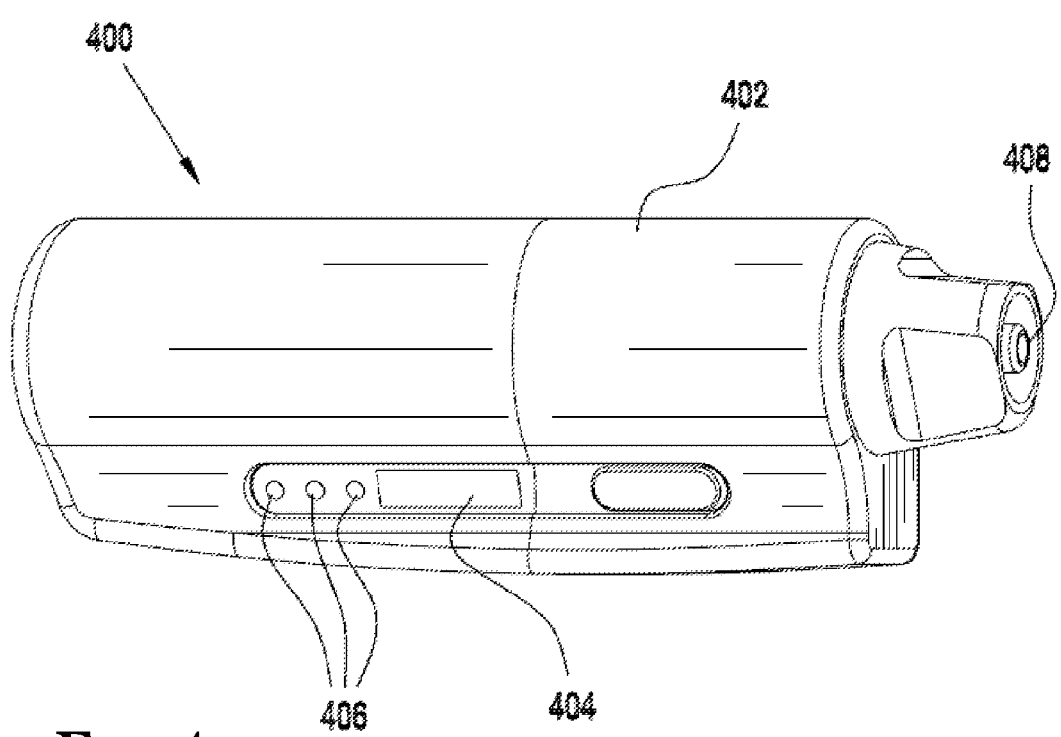

FIGS. 1A-3 illustrate a drive mechanism 100 of an infusion pump according to an exemplary embodiment of the present invention. Generally cylindrical in shape, the drive mechanism 100 includes a proximal end 102, a distal end 104 and a combined motor and gearbox (hereinafter referred to as a "motor 106") operatively coupled to a lead screw 108 that is configured to engage a piston 110. The proximal end 102 of the drive mechanism 100 is compliance mounted (i.e., has a "floating" mount) to an internal surface (not shown) of a housing of a drug delivery device such as, for example, an insulin pump. A compliance mount allows the motor housing to turn slightly in response to high motor torque during motor startup. The distal end 104 of the drive mechanism 100 is configured to engage a plunger 111 that is slidably inserted into a drug reservoir 112 (or cartridge) of a drug delivery device. The drive mechanism 100 is coaxially aligned or "in-line" with the axis of travel of the plunger 111. Embodiments of drug delivery devices that may be used with exemplary embodiments of the present invention are illustrated in FIGS. 4A and 4B.

The piston 110 includes a cavity 113 to receive the motor 106 and the lead screw 108 such that the lead screw 108 and at least a portion of the motor 106 are substantially contained within the piston cavity 113 when the piston 110 is in a retracted position. At least a portion of the motor 106 is also substantially contained within a cavity 114 of the lead screw 108 regardless of whether the piston 110 is in the retracted or extended position. In this embodiment, the length of the motor 106 is greater than a diameter of the motor 106. The length of the motor 106 is from about 20 millimeters to about 30 millimeters and the diameter of the motor is from about 5 millimeters to about 10 millimeters. This configuration of the piston 110, lead screw 108 and motor 106 results in a more compact drug delivery device than with conventional motor configurations which are parallel to the axis of travel of the plunger.

An outer surface 116 of the piston 110 further includes a keying feature 118 that mates with a slot (not shown) in the internal surface of the housing of the drug delivery device. The keying feature 118 prevents rotation of the piston 110 during use of the drive mechanism 100 such that the piston 110 moves only in the axial direction A.

The motor 106 is coupled to and drives a drive shaft 120, which is coupled via a hub to an inner surface 124 of a first end 126 of the lead screw 108. The motor 106 is housed within and is attached to a motor mounting sleeve 128 by at least one dowel pin 130. The motor mounting sleeve 128 prevents the motor 106 from rotating by being keyed (not shown) to a base mount 132 that is attached to an internal surface of the drug delivery device. The base mount 132 radially surrounds the motor mounting sleeve 128 near a proximal end 134 of the motor mounting sleeve 128. A plurality of linear bearings 136 between the motor mounting sleeve 128 and the base mount 132 allow the motor mounting sleeve 128 to "float" axially such that a force sensor 138 can sense a load on the motor 106 when, for example, the infusion line that delivers the drug from the drug reservoir is occluded. The force sensor 138 is coupled to a force sensor contact 140 at the proximal end 134 of the motor mounting sleeve 128.

The lead screw 108 includes external threads 142 that mate with internal threads 144 of the piston 110. Radial bearings 146 that allow rotational movement of the lead screw 108 may be included in a space 148 between a second end 150 of the lead screw 108 and an outer surface 152 of the motor mounting sleeve 128.

In use, the torque generated from the motor 106 is transferred to the drive shaft 120, which then rotates the lead screw 108. As the lead screw 108 rotates, the external threads 142 of the lead screw 108 engage with the internal threads 144 of the piston 110, causing the piston 110 to move in the axial direction A from a retracted position (see FIG. 1B) to an extended position (see FIG. 3). As the piston 110 moves from the retracted position to the extended position, the distal end of the piston 110 engages the plunger 111 (shown in FIG. 2) such that the drug is delivered from the drug reservoir or cartridge.

Referring to FIGS. 4A and 4B, drug delivery devices 300 and 400 that may be used with embodiments of the present invention each include a housing 302 and 402, respectively, a display 404 (not shown in device 300) for providing operational information to the user, a plurality of navigational buttons 306 and 406 for the user to input information, a battery (not shown) in a battery compartment for providing power to drug delivery devices 300 and 400, processing electronics (not shown), drive mechanism 100 for forcing a drug from a drug reservoir through a side port 308 and 408 connected to an infusion set (not shown) and into the body of the user.

Figure 5A:
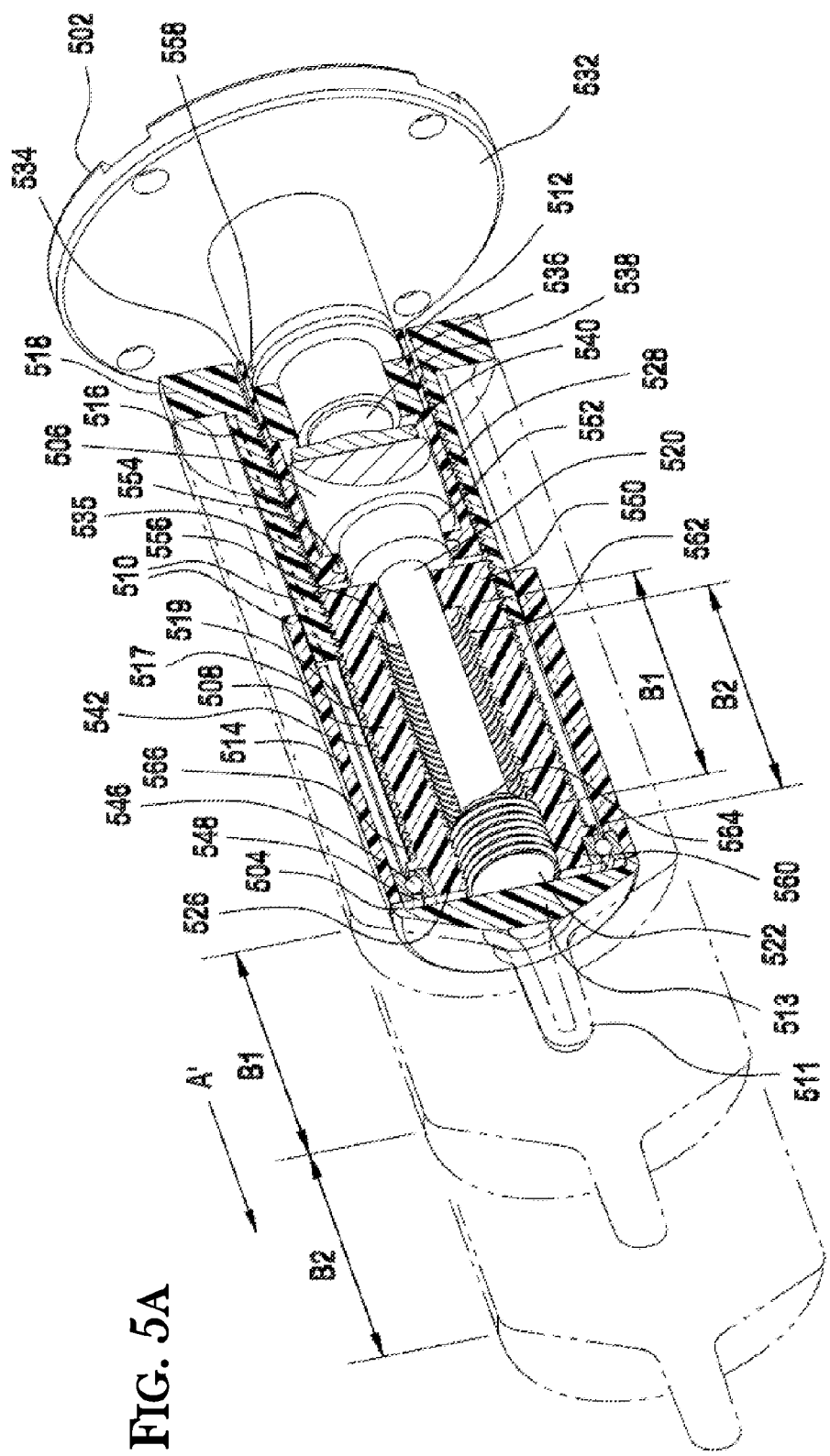
FIGS. 5A-5C are cross-sectional perspective views of an in-line drive mechanism according to another embodiment of the present invention with the piston in retracted, intermediate and extended positions, respectively.
Figure 5B:
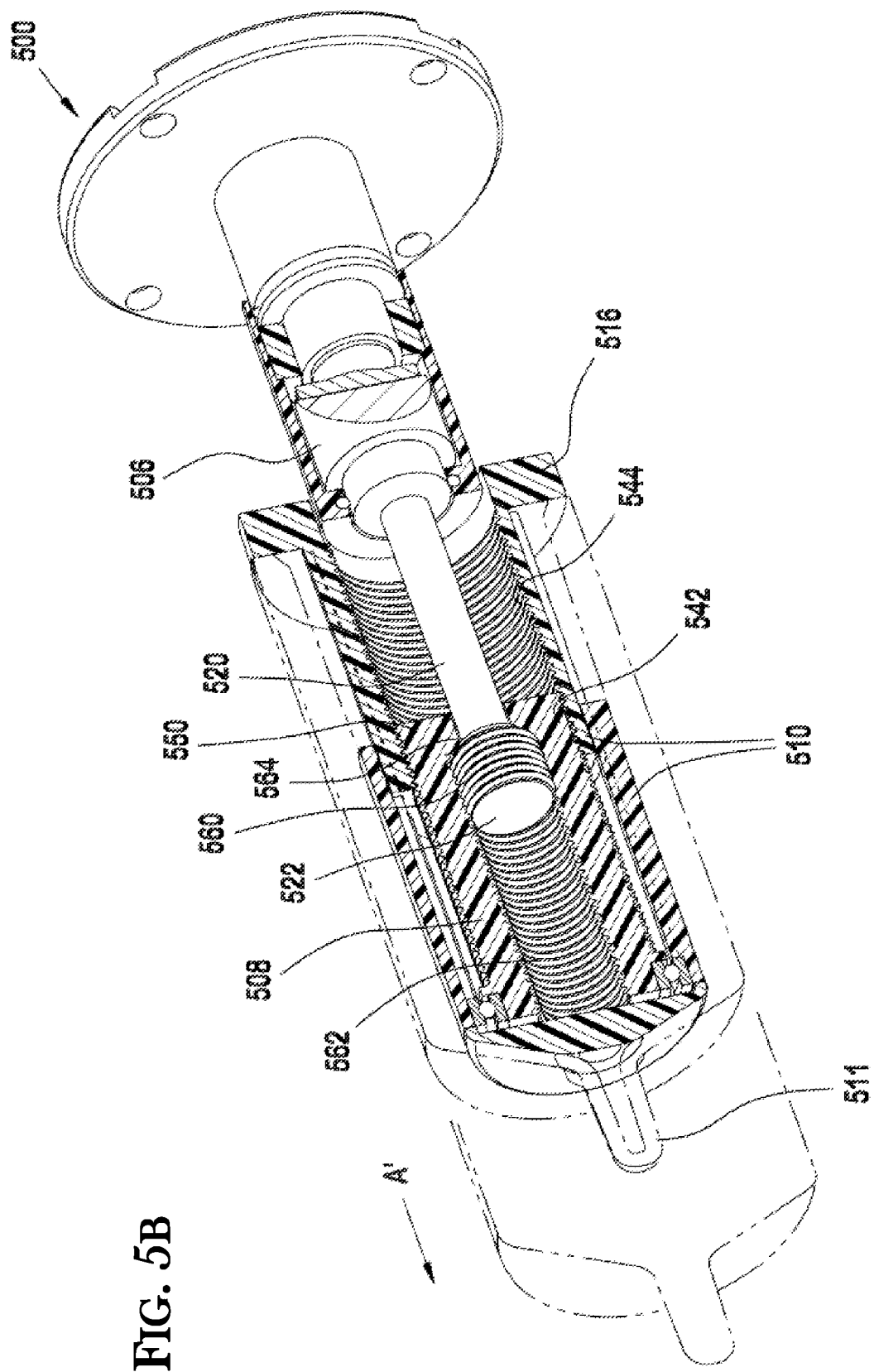
Figure 5C:
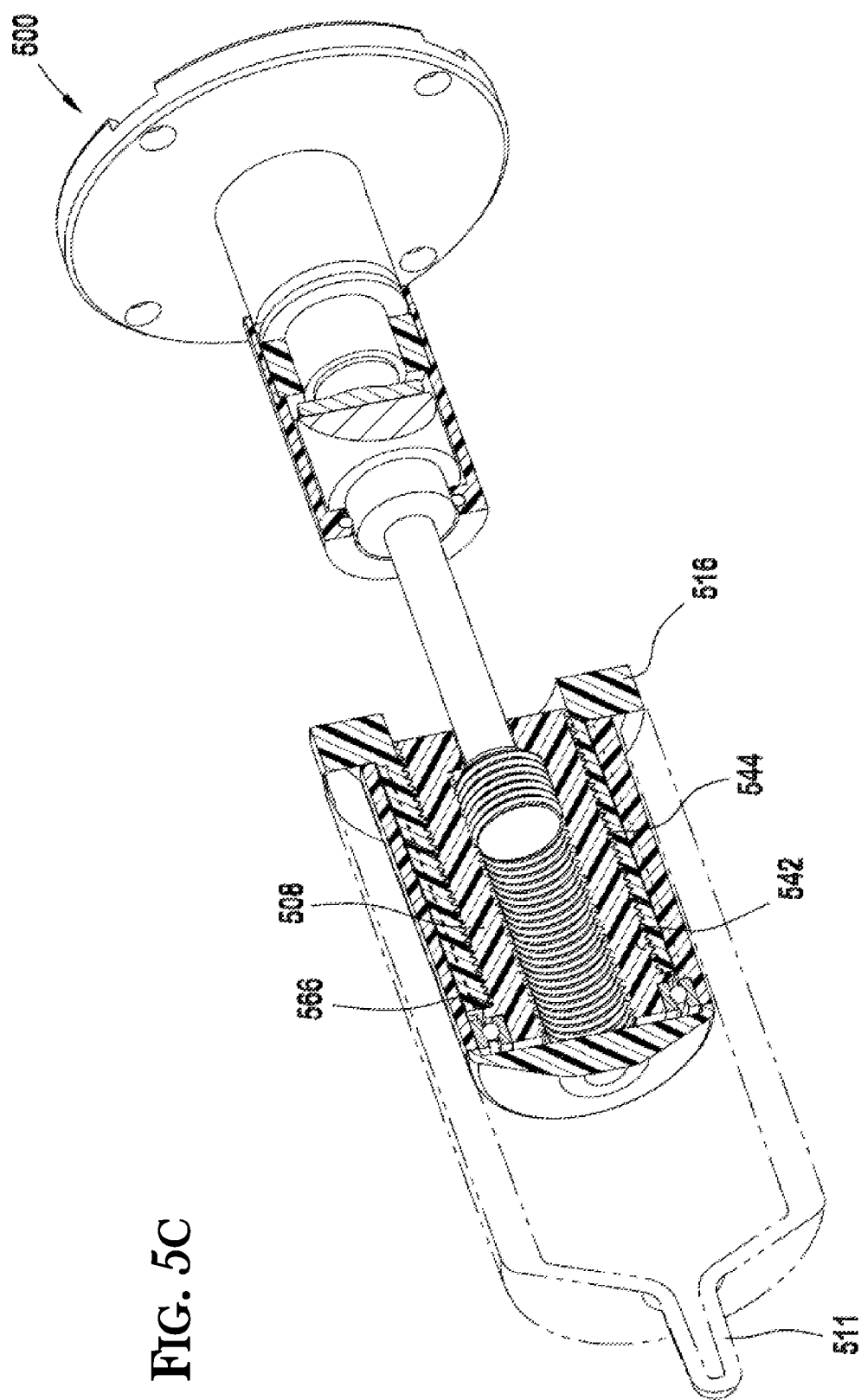

Referring now to FIGS. 5A-5C, another embodiment of the present invention is illustrated. The drive mechanism 500 is cylindrical in shape and includes a proximal end 502, a distal end 504 and a motor 506 operatively coupled to a lead screw 508, which is configured to engage a piston 510. The proximal end 502 of the drive mechanism 500 is compliance mounted to an internal surface (not shown) of a housing of a drug delivery device. The distal end 504 of the drive mechanism 500 is configured to engage a plunger 511 that is slidably inserted into a drug reservoir of a drug delivery device. The drive mechanism 500 is coaxially aligned or "in-line" with the axis of travel of the plunger.

The piston 510 includes a cavity 512 to receive the motor 506 and the lead screw 508 such that the lead screw 508 and the motor 506 are substantially contained within the piston cavity 512 when the piston 510 is in a retracted position. In this embodiment, the piston 510 and lead screw 508 have a "telescoping" configuration, as will be described in more detail below. The piston 510 includes a cap 513, a first member 514 and a second member 516. The cap 513 is affixed to the first member 514. At least one spline 517 on an inner surface 519 of the first member 514 mates with at least one groove (not shown) on an outer surface of the second member 516. The at least one spline 517 prevents rotational movement of the first member 514 such that the first member 514 only moves in an axial direction A'. The second member 516 is at least partially slidably inserted into the first member 514 and includes internal threads 544 that mate with external threads 542 on the lead screw 508. The second member 516 includes a keying feature 518 (e.g., a flange) on a proximal end that mates with a slot (not shown) on an inner surface of the drug delivery device housing. The keying feature 518 prevents rotation of the second member such that the second member only moves in the axial direction A'.

In this embodiment of the drive mechanism 500, the motor 506 is a "flat" motor with the diameter being greater than the length. The length of the motor is from about 2 millimeters to about 12 millimeters and the diameter of the motor is from about 10 millimeters to about 15 millimeters. The configuration of the piston 510, lead screw 508 and motor 506 results in a more compact drug delivery device than with conventional motor configurations, which are parallel to the axis of travel of the plunger.

The motor 506 drives a drive shaft 520, which is coupled to a drive nut 522. The motor 506 is housed within and is attached to a motor mounting sleeve 528. The motor mounting sleeve 528 prevents the motor 506 from rotating by being keyed (not shown) to a base mount 532 that is attached to an internal surface of the drug delivery device. The base mount 532 is nested inside the motor mounting sleeve 528 near the proximal end 534 of the motor mounting sleeve 528. A plurality of linear bearings 536 between the motor mounting sleeve 528 and the base mount 532 allow the motor mounting sleeve 528 to "float" axially such that a force sensor 538 can sense a load on the motor 506 when, for example, the infusion line that delivers the drug from the drug reservoir is occluded. The force sensor 538 is coupled to a force sensor contact 540 at the proximal end of the motor 506.

A distal end 535 of the motor mounting sleeve 528 is located adjacent to a second end 550 of the lead screw 508 when the piston 510 is in a retracted position. In order for the drive shaft 520 to connect to the drive nut 522, the drive shaft 520 protrudes through an opening 552 in the distal end 535 of the motor mounting sleeve 528. A first dynamic radial seal 554 is located between the drive shaft 520 and the motor mounting sleeve 528 to prevent fluid from contacting the motor 506. The first dynamic radial seal 554 allows axial movement of the motor mounting sleeve 528 for force sensing. The static radial seal 554 may be formed from a low friction material such as, for example, Teflon. In the embodiment shown in FIGS. 5A and 5B, the drive nut 522 spans the longitudinal distance from the first end 526 to the second end 550 inside a lead screw cavity 556. In an alternative embodiment, the drive nut 522 spans a portion of the distance from the first end 526 to the second end 550 inside the lead screw cavity 556 and the length of the drive shaft 520 is increased accordingly.

A dynamic radial seal 558 may also be located between the base mount 532 and the motor mounting sleeve 528 to prevent fluid from reaching the motor 506. The dynamic radial seal 558 allows axial movement of the motor mounting sleeve 528 for force sensing. The dynamic radial seal 558 may be formed from a low friction material such as, for example, Teflon.

The drive nut 522 includes external threads 560 that mate with internal threads 562 of the lead screw 508. The lead screw 508 also includes external threads 542 that mate with internal threads 544 of the second member 516 of the piston 510. Radial bearings 546 may be included in a space 548 between the first end 526 of the lead screw 508 and an inner surface of the first member 514 of the piston 510 to allow rotation of the lead screw 508.

In use, the torque generated from the motor 506 is transferred to the drive shaft 520, which then rotates the lead screw 508. As the lead screw 508 rotates, the external threads 560 of the drive nut 522 engage with the internal threads 562 of the lead screw 508 such that the lead screw 508 moves first distance B1 in an axial direction until a first stop 564 on the drive nut 522 is engaged with an internal surface of the second end 550 of the lead screw 508, as illustrated in FIG. 5B. Because the external threads 542 near the second end 550 of the lead screw 508 are engaged with the internal threads 544 of the second member 516 of the piston 510 and the piston 510 can only move axially, the piston 510 also moves first distance B1. Next, the external threads 542 of the lead screw 508 engage with the internal threads 544 of the second member 516 of the piston 510, causing the piston 510 to move a second distance B2 in an axial direction until a second stop 566 on an external surface of the lead screw 508 is engaged, as illustrated in FIG. 5C. Thus, the piston 510 moves from a retracted position (see FIG. 5A) to a fully extended (or telescoped) position (see FIG. 5C). As the piston 510 moves from the retracted to the extended position, the distal end of the piston 510 engages the plunger 511 such that the drug is delivered from the drug reservoir or cartridge. Because the internal and external threads of the components in the drive mechanism 500 have the same pitch, the order in which the components move axially is not critical to the function of the drive mechanism 500.

Figure 6A:
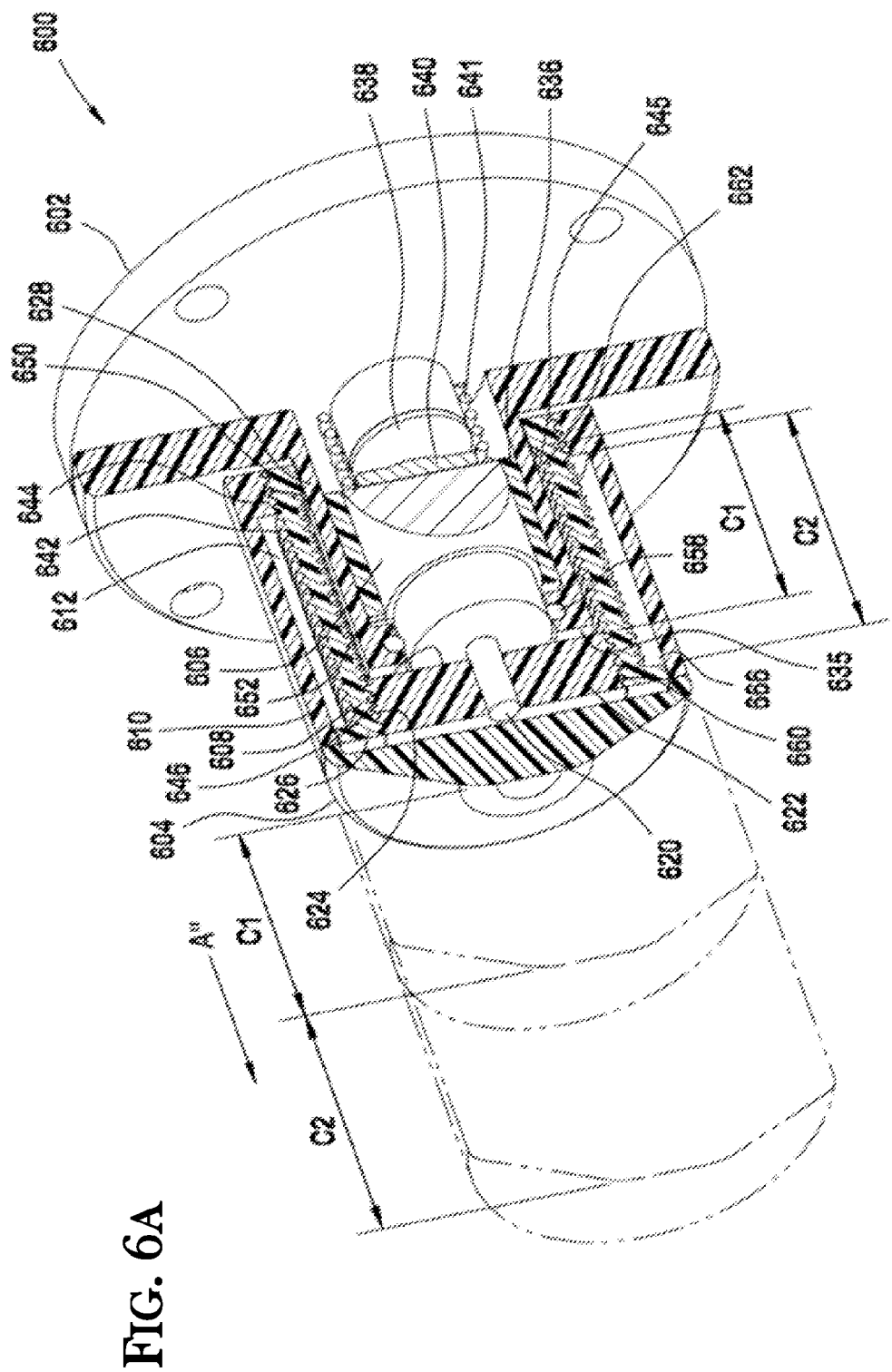
FIGS. 6A-6C are cross-sectional perspective views of an in-line drive mechanism according to yet another embodiment of the present invention with the piston in retracted, intermediate and extended positions, respectively.
Figure 6B:
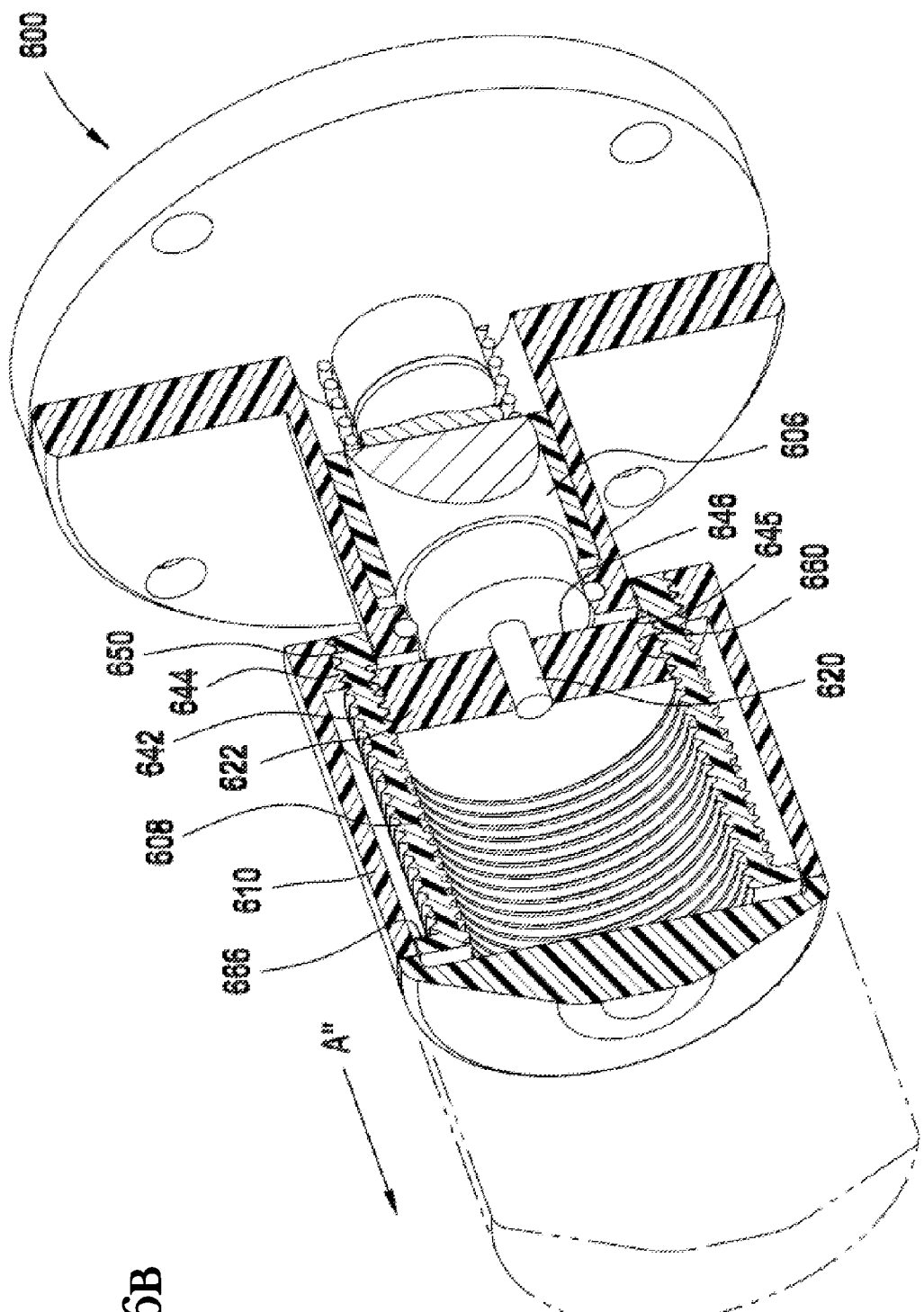
Figure 6C:
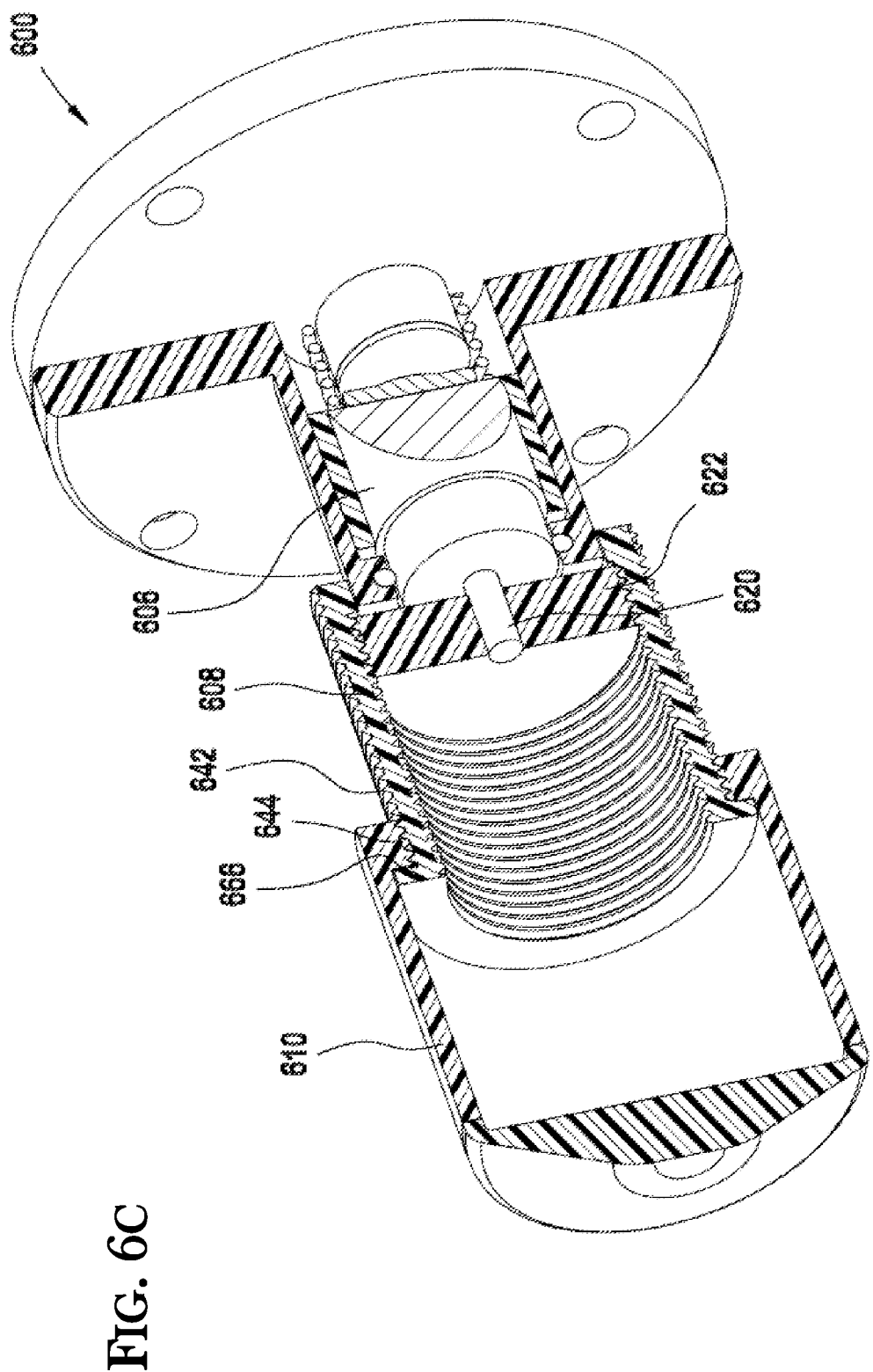

FIGS. 6A-6C illustrate yet another embodiment of the present invention. The drive mechanism 600 is cylindrical in shape and includes a proximal end 602, a distal end 604 and a motor 606 operatively coupled to a lead screw 608 that is configured to engage a piston 610. The proximal end 602 of the drive mechanism 600 is compliance mounted to an internal surface (not shown) of a housing of a drug delivery device. The distal end 604 of the drive mechanism 600 is configured to engage a plunger (not shown) that is slidably inserted into a drug reservoir of a drug delivery device. The drive mechanism 600 is coaxially aligned or "in-line" with the axis of travel of the plunger.

The piston 610 includes a cavity 612 to receive the motor 606 and the lead screw 608 such that the lead screw 608 and the motor 606 are substantially contained within the piston cavity 612 when the piston 610 is in a retracted position. In this embodiment, the piston 610 and lead screw 608 have a "telescoping" configuration, as will be described in more detail below. The piston 610 includes internal threads 644 near a proximal end that mate with external threads 642 on the lead screw 608. The piston 610 further includes a keying feature (not shown) on an outer surface of the proximal end that mates with a slot (not shown) on an inner surface of the drug delivery device housing. The keying feature prevents rotation of the piston 610 such that the piston 610 only moves in an axial direction A".

In this embodiment, the motor 606 is a "flat" motor with the diameter being greater than the length. The length of the motor 606 is from about 2 millimeters to about 12 millimeters and the diameter of the motor 606 is from about 10 millimeters to about 15 millimeters. The configuration of the piston 610, lead screw 608 and motor 606 results in a more compact drug delivery device than with conventional motor configurations which are parallel to the axis of travel of the plunger.

The motor 606 is coupled to and drives a drive shaft 620. The drive shaft 620 is coupled to a drive nut 622 to an inner surface 624 of a first end 626 of the lead screw 608. The motor 606 is housed within a motor mounting sleeve 628, which prevents the motor 606 from rotating by being affixed (not shown) to an internal surface of the drug delivery device. A plurality of linear bearings 636 located between the motor 606 and the motor mounting sleeve 628 allow the motor 606 to "float" axially such that a force sensor 638 can sense a load on the motor 606 when, for example, the infusion line that delivers the drug from the drug reservoir is occluded. The force sensor 638 is coupled to a force sensor contact 640 at the proximal end of the motor 606. A spring 641 may optionally be located between the motor 606 and the drug delivery device housing such that the motor 606 is biased away from the force sensor 638.

A distal end 635 of the motor mounting sleeve 628 is located adjacent to a second end 646 of the drive nut 622 when the piston 610 is in a retracted position. In order for the drive shaft 620 to connect to the drive nut 622, the drive shaft 620 protrudes through an opening 652 in the distal end of the motor mounting sleeve 628. A dynamic radial seal 658 is located between the drive shaft 620 and the motor mounting sleeve 628 to prevent fluid from contacting the motor 606. The dynamic radial seal 658 allows axial movement of the motor mounting sleeve 628 for force sensing. The dynamic radial seal 658 is formed from a low friction material such as, for example, Teflon.

The drive nut 622 includes external threads 660 that mate with internal threads 662 of the lead screw 608.

In use, the torque generated from the motor 606 is transferred to the drive shaft 620, which then rotates the lead screw 608. As the lead screw 608 rotates, the external threads 660 of the drive nut 622 engage with the internal threads 662 near the first end 626 of the lead screw 608 such that the lead screw 608 moves a first distance C1 in an axial direction until a surface 645 on the proximal end of the lead screw 608 engages the second end 646 of the drive nut 622, as illustrated in FIG. 6B. Because the external threads 642 near the second end 650 of the lead screw 608 are engaged with the internal threads 644 of the piston 610 and the piston 610 can only move axially, the piston 610 also moves the first distance C1 in an axial direction. Next, the external threads 642 near the second end 650 of the lead screw 608 engage with the internal threads 644 near the proximal end of the piston 610, causing the piston 610 to move a second distance C2 in an axial direction until a stop 666 on an external surface of the lead screw 608 is engaged, as illustrated in FIG. 6C. Thus, the piston 610 moves from a retracted position (see FIG. 6A) to a fully extended (or telescoped) position (see FIG. 6C). As the piston 610 moves from the retracted to the extended position, the distal end of the piston 610 engages the plunger such that the drug is delivered from the drug reservoir or cartridge. Because the internal and external threads of the components in the drive mechanism 600 have the same pitch, the order in which the components move axially is not critical to the function of the drive mechanism 600.

An advantage of the telescoping arrangement illustrated in FIGS. 6A-6C is that the length of the piston 610 can be reduced by about 40% (or distance C1 in FIG. 6A) versus non-telescoping configurations, resulting in a more compact drug delivery device.

The motors depicted in FIGS. 1-6B may optionally include an encoder (not shown) that, in conjunction with the electronics of the drug delivery device, can monitor the number of motor rotations. The number of motor rotation can then be used to accurately determine the position of the piston, thus providing information relating to the amount of fluid dispensed from the drug reservoir.

In each of the previously described embodiments, the drive components are forced to stall when the driving elements bind against the static elements. The component is then backed-off of the stall situation. This method of interaction between the driving and static components requires additional energy resulting from the increased motor current to drive the mechanism into a stall. Further, binding stress can, over time, weaken or deform the components; and the free-floating lead screw may, if the pump is impacted, heated, cooled or exposed to any other conditions which may loosen the stalled lead screw, can result in reduced infusion accuracy, particularly if the lead screw begins to rotate opposite to the drive nut. When this occurs, the motor turns without producing any forward movement of the piston.

The embodiment of the telescoping drive mechanism shown in FIGS. 7-8 may have certain advantages regarding delivery accuracy and reduced power consumption. This embodiment employs a structure that eliminates the requirement that the components bind in order to transfer rotational energy from one component to another. As illustratively shown in FIG. 7, one embodiment of the present invention relates to a medicament infusion device 700 with drive mechanism 710 that engages a drive shaft 730. In this instance, the drive shaft 730 is keyed to engage gearshaft 735 to impart rotational energy from the drive mechanism 710 which may include a motor and gear assembly, to the drive shaft 730.

The drive shaft 730 is enclosed within, but rotationally independent from the compound threaded lead screw 750. Rotation of the drive shaft 730 turns the threaded piston 755. External threads on the compound threaded lead screw 750 engage corresponding threads on an internal surface of the threaded piston 755 to result in lateral movement of the threaded piston 755 relative to compound threaded lead screw 750. This motion can either advance the threaded piston and push the cartridge plunger 740 into the cartridge cavity 760, thereby expelling medicament via outlet port 770.

Expanding of this mechanism is the ability of the threaded piston 755 and compound threaded lead screw 750 to cooperate with each other and a threaded housing 765 with, as shown in FIGS. 7C and 7D, an internal threaded wall. For example, the motor and gear box that comprise the drive mechanism 710 turn the keyed drive shaft 730 clockwise which interfaces with and turns the compound threaded lead screw 750 clockwise in a one-to-one manner.

The threading on the lower, wider section of the compound lead screw 750 interfaces with the threading on the threaded housing 765. As the compound lead screw rotates clockwise it is driven upward with respect to the threaded housing, due to the engagement of the meshing threads and their relative motion with respect to one another. As the compound threaded lead screw 750 is driven upward it freely slides along the length of the keyed drive shaft 730.

The threading on the upper, thinner section of the compound threaded lead screw 750 interfaces with the threading on the threaded piston 755. As the compound threaded lead screw 750 rotates clockwise, the threaded piston 755 is driven upward with respect to the compound lead screw. The threaded piston 755 is fixed rotationally using keyways in the housing collar 775. The housing collar 755 is disposed between the upper section of the compound threaded lead screw 750 and the inner diameter of the threaded housing 765 and is in turn fixed rotationally by a keyway in the threaded housing, shown in the enlarged view in FIG. 8C.

The telescoping nature of this piston mechanism results from the threaded piston 755 being driven upward with respect to the compound threaded lead screw 750 while simultaneously the compound threaded lead screw 750 is being driven upward with respect to the threaded housing 765. In one embodiment the drive mechanism 710 is biased against a force sensor plate 780. During operation, occlusions within the fluid delivery system may increase the back pressure of the cartridge plunger 740 against the threaded piston 755. In turn, this pressure is translated through the drive shaft 730 to the drive mechanism 710 and is perceived as increased pressure on the force sensor plate 780. A force sensor in communication with the force sensor plate 780 may then register an increase in pressure that can be indicative of an occlusion in the fluid delivery system.

The telescoping piston drive mechanism may comprise five individual pieces: the threaded housing 765, the housing collar 755, the threaded piston 755, the compound threaded lead screw 750 and the keyed driveshaft 730. FIGS. 7A-7D shows the fully assembled telescoping piston drive mechanism in retracted, partially extended and fully extended positions.

The threaded housing 765 is the outermost piece. It may be a generally hollow tube that is threaded on the interior along its entire length. The lower (wider) threaded portion of the compound threaded lead screw 750 is configured to interface with this threading. The threaded housing 765 is fixed to the pump body 700 and forms the base against which the telescoping piston drive mechanism is biased. Two vertical channels are cut into the interior to act as keyways to allow the collar to slide along the inside of the housing while constraining its rotational movement. This piece does not necessarily need to be a separate component—it may be molded as part of the base assembly thus reducing the overall number of components in the pump.

The housing collar 775 may be a hollow tube with no threading. It is designed to fit within the threaded housing 765 and rest on top of the compound threaded lead screw 750. It has keys near the bottom of the exterior to interface with the keyways in the housing thus allowing linear movement while constraining rotational movement, as shown in cross-sectional view in FIG. 8C.

The threaded piston 755 may be a generally hollow tube which is threaded on the interior. This threading is opposite to that of the housing (i.e. clockwise vs. counterclockwise). The upper (thinner) threaded portion of the compound threaded lead screw 755 will interface with this threading. The top of the threaded piston 755 will interface with and drive the plunger 740 of the cartridge. The threaded piston 755 has two keys near the bottom of the exterior and is designed to fit within the housing collar 775 and interface with the keyways thus allowing linear movement while constraining rotational movement as illustrated in FIG. 8C.

The compound thread lead screw 7505 may be an inverse-T shaped shaft (i.e. a short wide diameter section at the bottom and a long narrow diameter section on top.) Both sections are threaded but in opposite directions. The lower, wider threaded section interfaces with the threading on the interior of the housing 765 while the upper, narrow threaded section interfaces with the threading on the interior of the piston 755. There can be a keyed slot (not shown) cut into the center of the compound lead screw 750 which will interface with a keyed shaft 730 which is driven by the motor 710. The compound lead screw 750 and the keyed shaft 730 can be the only components in the assembly that rotate. As the compound lead screw 750 rotates, it drives the piston 755 upward. Due to the threaded interaction between the compound lead screw 750 and the housing 765, the compound lead screw 750 is driven upward relative to the housing 765. This combination drives the piston 755 upward at a rate which is faster than the compound lead screw 750 is being driven upward, thus producing the telescoping effect.

The keyed driveshaft 730 transfers the rotational energy from the motor 710 to the compound lead screw 750 while allowing the compound lead screw 750 to translate linearly. The keyed driveshaft 730 may rotate, but it does not move linearly.

The housing 765, collar 775, and piston 755 will generally be injection molded in polycarbonate or other high-durability plastics, such as Delrin (DuPont), a polyoxymethylene (POM), which is an engineering thermoplastic used in precision parts that require high stiffness, low friction and excellent dimensional stability. The compound lead screw 750 and keyed drive shaft 730 can be machined or cast in medical-compatible stainless steel, brass, aluminum or other readily machined metals. Alternatively the housing 765, collar 775, and piston 755 may be machined or cast in metals which are similar to the compound lead screw 750 and keyed drive shaft 730. This may improve the overall reliability of the drive mechanism and precision of the delivery due to the relative elastic modulus comparatively between metals and plastics. However, this would also increase the cost of the mechanism. Conversely, the compound lead screw 750 and keyed drive shaft 730 may be injection molded in a similar plastic as the housing 765, collar 775, and piston 755. This would decrease the overall cost of the drive mechanism, however the mechanism would have a shorter end-of-life and may offer less precision of delivery due to the relative elastic modulus comparatively between metals and plastics.

It will be recognized that equivalent structures may be substituted for the structures illustrated and described herein and that the described embodiment of the invention is not the only structure, which may be employed to implement the claimed invention. In addition, it should be understood that every structure described above has a function and such structure can be referred to as a means for performing that function. While embodiments of the present invention have been shown and described herein, it will be obvious to those skilled in the art that such embodiments are provided by way of example only. Numerous variations, changes, and substitutions will now occur to those skilled in the art without departing from the invention.

It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A medicament infusion device, comprising:
   a housing having an interior surface, the interior surface of the housing being at least partially threaded;
   a cavity within the housing configured to receive a cartridge, the cartridge having a reservoir for holding a medicament, a plunger for expelling the medicament from the reservoir, and an outlet port at a distal end of the housing;
   a drive mechanism disposed at a proximal end of the housing;
   a drive shaft in cooperation with the drive mechanism;
   a compound lead screw, the compound lead screw being essentially cylindrical and having at least a portion having a first diameter and at least a portion having a second diameter, wherein each of the portion having the first diameter and the portion having the second diameter are threaded, and the second diameter is greater than the first diameter;
   a piston having at least one threaded surface;
   at least one keyway, wherein the at least one keyway is configured to permit lateral motion of one of the compound lead screw or piston without permitting rotational motion; and
   and wherein the at least partially threaded interior surface of the housing engages the threaded second diameter of the compound lead screw and the compound lead screw moves relative to the at least partially threaded interior surface of the housing upon a rotation of the compound lead screw;
   wherein the threaded surface of the piston engages the threaded portion of the first diameter of the compound lead screw; and
   wherein the at least one threaded surface of the piston is an internal surface.

2. The medicament infusion device of claim 1 further comprising a housing collar disposed between an upper section of the compound threaded lead screw and the interior surface of the housing and wherein the at least one keyway rotationally fixes the housing collar within the housing.

3. The housing collar of claim 2, the housing collar having an essentially circular cross-sectional profile and having two keyways, wherein the two keyways are arranged on substantially opposite side of the circumference of the housing collar.

4. The medicament infusion device of claim 2 comprising a force sensor plate disposed adjacent to the drive mechanism.

5. The medicament infusion device of claim 4 comprising a force sensor in communication with the force sensor plate.

6. The medicament infusion device of claim 5 wherein the force sensor is in electronic communication with the drive mechanism.

7. The medicament infusion device of claim 2 wherein rotation of the drive shaft produces motion of the plunger into the cartridge cavity.

* * * * *